(12) United States Patent
Harada et al.

(10) Patent No.: US 9,326,946 B2
(45) Date of Patent: May 3, 2016

(54) LAMINATED TABLET AND MANUFACTURING METHOD THEREFOR

(75) Inventors: Kazuki Harada, Osaka (JP); Hikaru Fukuyama, Osaka (JP); Masahiko Koike, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/002,451

(22) PCT Filed: Mar. 2, 2012

(86) PCT No.: PCT/JP2012/055382
§ 371 (c)(1),
(2), (4) Date: Oct. 10, 2013

(87) PCT Pub. No.: WO2012/118180
PCT Pub. Date: Sep. 7, 2012

(65) Prior Publication Data
US 2014/0023708 A1    Jan. 23, 2014

(30) Foreign Application Priority Data
Mar. 3, 2011    (JP) .................. 2011-046617

(51) Int. Cl.
*A61K 9/20* (2006.01)
*A61K 9/24* (2006.01)
*A61K 45/06* (2006.01)

(52) U.S. Cl.
CPC .............. *A61K 9/2095* (2013.01); *A61K 9/209* (2013.01); *A61K 9/2072* (2013.01); *A61K 9/2086* (2013.01); *A61K 45/06* (2013.01)

(58) Field of Classification Search
None
See application file for complete search history.

(56) References Cited

U.S. PATENT DOCUMENTS

| 7,838,031 B2 * | 11/2010 | Solomon et al. ............... 424/467 |
| 2002/0147125 A1 | 10/2002 | Hoflinger et al. |
| 2006/0165777 A1 | 7/2006 | Solomon et al. |
| 2008/0299197 A1 * | 12/2008 | Toneguzzo et al. ........... 424/473 |
| 2009/0018043 A1 | 1/2009 | Beckers et al. |
| 2009/0110726 A1 * | 4/2009 | Narasaki et al. ............... 424/467 |
| 2010/0239668 A1 | 9/2010 | Kaplan et al. |
| 2011/0244040 A1 * | 10/2011 | Ono et al. ...................... 424/474 |

FOREIGN PATENT DOCUMENTS

| EP | 1915988 A1 | 4/2008 |
| EP | 2 329 812 A1 | 6/2011 |
| JP | 08-277218 A | 10/1996 |
| JP | 2008-255064 A | 10/1996 |
| JP | 2007-020929 A | 2/2007 |
| JP | 2008-500401 A | 1/2008 |
| JP | 2008-208078 A | 9/2008 |
| JP | 2009-541341 A | 11/2009 |
| WO | WO 2005/016306 A2 | 2/2005 |
| WO | WO 2006/089493 A1 | 8/2006 |
| WO | WO 2006/099618 A1 | 9/2006 |
| WO | WO 2010/032717 A1 | 3/2010 |
| WO | WO2010032717 | * 3/2010 ............... A61K 9/28 |

* cited by examiner

*Primary Examiner* — Bethany Barham
*Assistant Examiner* — Ping Cao
(74) *Attorney, Agent, or Firm* — Foley & Lardner LLP

(57) ABSTRACT

According to the present invention, a multilayer tablet showing suppressed layer separation and a production method thereof are provided. A concave portion having a depth of not less than 0.1 mm Ka is formed on at least one surface Sa of the both front and back surfaces (Sa, Sb) of a multilayer tablet. Particularly, a multilayer structure obtained by, in tableting, forming a convex portion for forming the concave portion on at least the upper punch, and preliminarily compressing all layers in the multilayer tablet with the upper punch to form a concave portion having the same shape with a depth of not less than 0.1 mm on the upper surface of all layers, wherein the powder materials of the next layer are protruding into the concave portion, is a preferable embodiment.

6 Claims, 7 Drawing Sheets

(a)

(b)

(a)

(b)

(a)

(b)

(c)

(d)

LAMINATED TABLET AND MANUFACTURING METHOD THEREFOR

TECHNICAL FIELD

The present invention relates to a multilayer tablet and a production method thereof.

BACKGROUND OF THE INVENTION

Multilayer tablet (also called a multilayered tablet and the like) is a tablet having a multilayer structure consisting of two or more layers, which is used as, for example, one of the dosage forms for combination drugs (patent document 1).

Multilayer tablet can be formed by compressing (tableting) powder materials, which is similar to the case of general core tablets and the like. FIG. 6 is a sectional view of a tableting apparatus, which schematically shows the manner of formation of a multilayer tablet by tableting, wherein a bilayer tablet is produced by tableting as an example.

As shown in FIG. 6(A), one set of a cylindrical shaped die Q10 and the upper and lower punches (upper punch P10 and lower punch P20) is set on a rotary table T10. As shown in the subsequent FIG. 6(B)-(G), while the set of the die and the punches proceeds according to the rotation of the table, stepwise feeding of powder materials into the die, preliminary compression by the upper and lower punches after each feeding, and then final main compression are performed. The completed bilayer tablet 300 is taken out. This series of manufacturing processes is explained in more detail as follows.

First, as shown in FIG. 6 (B), a predetermined amount of a powder material 100 for the first layer is fed from a hopper H10 into a space defined by a lower punch P20 and a die Q10 and, as shown in FIG. 6(C), the upper punch P10 descends following a roll R110, and the powder material 100 is preliminarily compressed by a lower punch P20 supported by a roll R120 and the above-mentioned upper punch P10 to form the first layer 110 in an intermediately-compressed state.

In the example of FIG. 6, a pressing surface of both the upper punch P10 and the lower punch P20 is concave-shaped, namely, both surfaces of a tablet are swollen, forming a convex shape. In this example, therefore, an upper surface of the first layer 110 has a convex-shaped curved surface by being pressed by a concave-shaped pressing surface of the upper punch P10.

Then, as shown in FIG. 6(D), a predetermined amount of a powder material 200 for the second layer is fed from a hopper H20 into a space defined by an upper surface of the first layer 110 and the die Q10 and, as shown in FIG. 6(E), the upper punch P10 descends following a roll R210, and the powder material 200 is preliminarily compressed by the lower punch P20 supported by the roll R120 and the above-mentioned upper punch P10 to form the second layer 210 in an intermediately-compressed state. An upper surface of the second layer 210 is also an upper surface of the whole tablet and, like the upper surface of the first layer 110, has a concave-shaped curved surface by being pressed by the pressing surface of the upper punch P10.

Furthermore, as shown in FIG. 6(F), the upper punch P10 descends following a roll R310 to the final position, and a multilayer body consisting of the first layer and the second layer is mainly compressed by the lower punch P20 supported by a roll R320 and the above-mentioned upper punch P10 to complete the object bilayer tablet 300. As shown in FIG. 6(G), the lower punch P20 rises for the bilayer tablet 300 to be taken out from the die.

One of the main objects of performing preliminary compression for each layer as mentioned above is to confirm the amount of the powder material fed for each layer, via the compressive stress during preliminary compression of each layer. For this end, an upper punch or a lower punch is provided with a load-cell for the stress measurement, and a constitution enabling measurement of the compressive stress upon displacement of the upper punch and/or the lower punch to a preliminary compression position specific to each layer is employed. Whether the volume of each layer (=amount of powder materials) shows variation beyond the defined range is observed through variation of the stress value.

As a result of the preliminary compression of each layer as mentioned above, the upper surface of the first layer 110 is formed first as a compression-packed surface of the powder materials as shown in FIG. 7(a) even though by preliminary compression, and the powder materials of the second layer 210 are compression packed later thereon, and therefore, an interface is formed between the layers, and the close adhesion force between the layers is comparatively low. Therefore, when a conventional bilayer tablet 300 is subject to an impact and the like, layer separation sometimes occurs as shown in FIG. 7(b). In the example of this Figure, the first layer 110 and the second layer 210 are separated at the interface (i.e., upper surface 110a of first layer 110, lower surface 210b of second layer 210).

Conventionally, to suppress such layer separation, for example, the close adhesion force between layers is increased by changing the formulation and powder properties.

However, the above-mentioned measures cannot suppress layer separation sufficiently.

DOCUMENT LIST

Patent Document

[patent document 1] JP-2008-255064-A1

SUMMARY OF THE INVENTION

Problems to be Solved by the Invention

The problem of the present invention is to solve the above-mentioned problem, and provide a multilayer tablet wherein layer separation is suppressed, and a production method thereof, and a method for suppressing layer separation of a multilayer tablet.

Means of Solving the Problems

The present inventors have conducted intensive studies in an attempt to solve the above-mentioned problems and found that the close adhesive force between layers becomes high when a concave portion having a particular depth or above is formed in at least one surface of a multilayer tablet, and the layer separation can be suppressed, which resulted in the completion of the present invention.

Accordingly, the present invention provides
(1) a multilayer tablet comprising a concave portion having a depth of not less than 0.1 mm formed on at least one surface of both the front and back surfaces of the multilayer tablet;
(2) the multilayer tablet of the above-mentioned (1), wherein a layer having the above-mentioned one surface having the concave portion is the top layer,
each of all layers other than the top layer has a concave portion with the same shape as the above-mentioned concave portion, in a top layer-side surface of the both surfaces of each layer, and the materials of the next layer are protruding into the concave portion;

(3) the multilayer tablet of the above-mentioned (1) or (2), wherein the above-mentioned concave portion is one or more groove-like concave portions;

(4) the multilayer tablet of any of the above-mentioned (1) to (3), wherein a groove-like concave portion is present along a straight line or a curve passing through the center point of one surface having the above-mentioned concave portion, when the surface is viewed straight on;

(5) the multilayer tablet of any of the above-mentioned (1) to (4), wherein the above-mentioned groove-like concave portion runs from one point on the outer circumference of the above-mentioned one surface, passes through the center point of the surface, and reaches a point on the opposite side of the outer circumference;

(6) the multilayer tablet of any of the above-mentioned (1) to (5), wherein the above-mentioned groove-like concave portion is a V-shaped groove;

(7) the multilayer tablet of the above-mentioned (6), wherein the above-mentioned V-shaped groove has an inside angle of the V-shape of 40 degrees-110 degrees;

(8) the multilayer tablet of any of the above-mentioned (2) to (7), wherein, of a pair of punches used in a tableting step, the upper punch which is a punch for pressing the above-mentioned one surface, has, on a mold surface thereof, a convex portion with a height of not less than 0.1 mm for forming the above-mentioned concave portion, all layers in said multilayer tablet are directly pressed by the same upper punch during successive tableting, whereby a concave portion having the same shape as the concave portion of the above-mentioned one surface is also formed in a top layer side surface of the both surfaces of each of all layers other than the above-mentioned top layer, and the materials of the next layer are protruding into the concave portion of each layer;

(9) a method of producing the multilayer tablet of the above-mentioned (1), comprising a step of sequentially laminating respective layers in the above-mentioned multilayer tablet on a mold surface of the lower punch, and tableting by an upper punch, at least the upper punch has a convex portion having a height of not less than 0.1 mm on its mold surface, the above-mentioned tableting step has a step of pressing all layers in said multilayer tablet by the above-mentioned upper punch, and the above-mentioned pressing step forms a multilayer structure wherein a concave portion having the same shape with a depth of not less than 0.1 mm is formed on an upper punch side surface of the both surfaces of all layers, and the materials of the next layer are protruding into the concave portions of all layers other than the top layer;

(10) a method for suppressing layer separation which is a method for suppressing layer separation of a multilayer tablet, comprising forming a concave portion having a depth of not less than 0.1 mm on at least one surface of both the front and back surfaces of the multilayer tablet;

(11) the method of the above-mentioned (10), wherein, when forming the above-mentioned multilayer tablet by sequentially laminating respective layers in a multilayer tablet on a mold surface of the lower punch, and tableting with the upper punch, at least the upper punch has, on its mold surface, convex portion having a height of not less than 0.1 mm, all layers in the above-mentioned multilayer tablet are pressed by the above-mentioned upper punch, whereby a multilayer structure wherein a concave portion having the same shape with a depth of not less than 0.1 mm is formed on an upper punch side surface of the both surfaces of all layers, and the materials of the next layer are protruding into the above-mentioned concave portions of all layers other than the top layer;

and the like.

Effect of the Invention

In the multilayer tablet of the present invention, in the same manner as in conventional methods in terms of the basic tableting steps, a first layer is formed in a die by preliminary compression, next layers are preliminary compressed for each layer thereon, and finally compressed mainly to give a multilayer body.

In the following, for the convenience of explanation, of the two sides of the multilayer tablet, the surface that can be formed by an upper punch in the tableting step is referred to as an "upper surface" and the surface on the opposite side of the "upper surface" is referred to as a "lower surface" of the tablet to set an up-and-down direction in the stack direction of the multilayer tablet for explanation. According to the up-and-down direction, the respective two sides of the respective layers in a multilayer tablet are also referred to as an "upper surface of the layer" and a "lower surface of the layer".

In the tableting step, the first layer formed on a lower punch in a die by preliminary compression is referred to as a "bottom layer" or "first layer", and the layers formed thereon are sequentially referred to by numbers such as "second layer", "third layer", . . . , "n-th layer", and the "n-th layer" to be finally formed is referred to as "top layer". In addition, a layer located immediately above and directly adjacent to one layer located on a lower side is referred to as a "next layer".

In the present invention, a concave portion is characteristically formed on "at least one surface" of the both obverse and reverse sides of a multilayer tablet. While the surface on which a concave portion is always formed may be any of the front and the back surfaces, in a more preferable embodiment, a concave portion is formed on an upper surface, which is a surface formed by an upper punch in the tableting step, to improve the close adhesive force between layers the suppress layer separation.

That is, as shown in the example of a trilayer tablet in FIG. 2, forming a concave portion Ka on an upper surface Sa of a multilayer tablet M means forming a convex portion Pk corresponding to the concave portion Ka on a pressing-surface Ps of the upper punch P1 during tableting. When such convex portion is formed on a pressing-surface of the upper punch, since each layer is preliminarily compressed in the tableting step, not only an upper surface Sa (=S3a) of the top layer L3 but also similar concave portions K1, K2 are formed on the upper surface of each layer (upper surface S1a of first layer L1, and upper surface S2a of second layer L2, respectively) by the preliminary compression, and the powder materials of the next layer protrude into each concave portion and compression packed to increase the close adhesion force between the two layers.

BRIEF DESCRIPTION OF THE DRAWINGS

FIG. 4 shows examples of the pattern drawn by the concave portion when the surface on which the concave portion is formed (upper surface of the examples in this Figure) is viewed straight on.

DETAILED DESCRIPTION OF THE INVENTION

In the following, the structure and production method of the multilayer tablet of the present invention, and a method for suppressing layer separation are explained by referring to the Figures.

Figure 1:
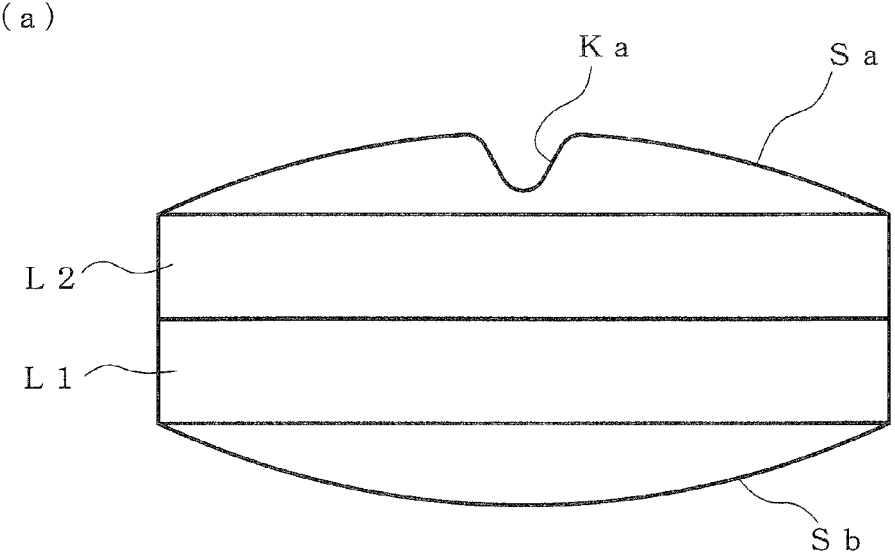
FIG. 1 shows one embodiment of the multilayer tablet of the present invention.
Figure 1:
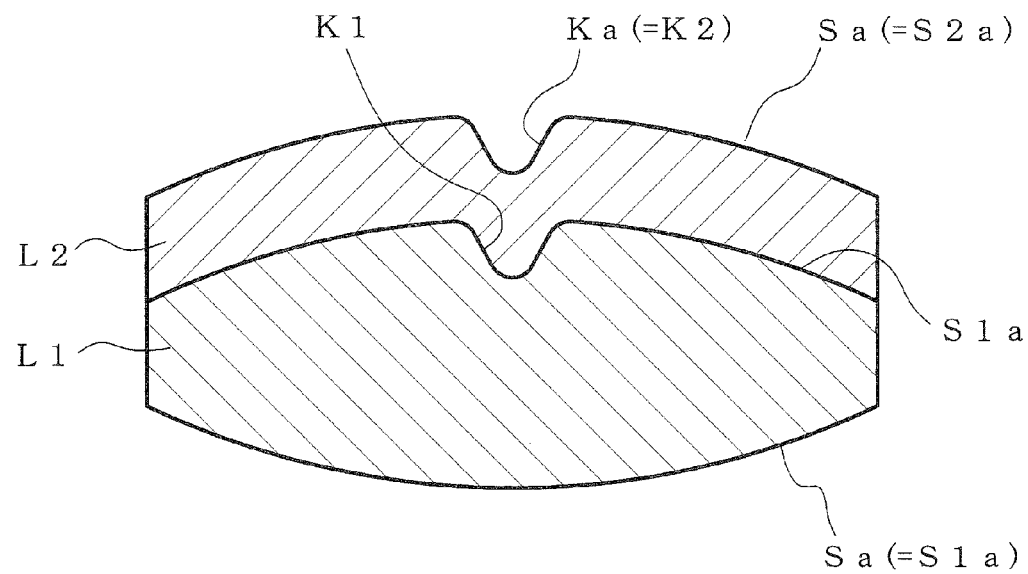

FIG. 1 schematically shows one example of the structure of the multilayer tablet. In the example of this Figure, the structure of a bilayer tablet consisting of the first layer L1 and the second layer L2 is shown. As shown in FIG. 1(b), the upper surface Sa of the multilayer tablet as a whole is also the upper surface S2a of the second layer L2, and similarly, the lower surface Sb of the multilayer tablet as a whole is also the lower surface S1b of the first layer L1.

As shown in FIG. 1(a), the multilayer tablet has a concave portion Ka having a depth of not less than 0.1 mm on at least one surface of both the front and back surfaces thereof (upper surface Sa in the example of this Figure), whereby the layer separation is suppressed.

This Figure also shows the method for suppressing layer separation of the present invention. In said method, a concave portion having a depth of not less than 0.1 mm is formed on at least one surface of both the front and back surfaces of a multilayer tablet, and the formation of the concave portion increased the close adhesion force between layers, whereby the layer separation is suppressed.

As stated in the explanation on the above-mentioned action, in a more preferable embodiment, the concave portion Ka is formed on an upper surface Sa formed by an upper punch so as to improve the adhesive force between layers. In the example of FIG. 1(b), a concave portion Ka (=concave portion K2 of second layer L2) is formed on the upper surface S2a(=Sa) of the second layer L2, which is the top layer, and also, a concave portion K1 is formed on the upper surface S1a of the first layer L1 by preliminary compression. That is, as shown in FIG. 2, when the concave portion Ka is formed on the upper surface Sa, concave portions K1, K2 having the same shape as the concave portion Ka are formed on the upper surfaces S1a, S2a of the all layers L1, L2 other than the top layer L3 by the preliminary compression with the upper punch, and the powder materials of the next layer protrude into the concave portion to increase the adhesive force between layers.

Figure 2:
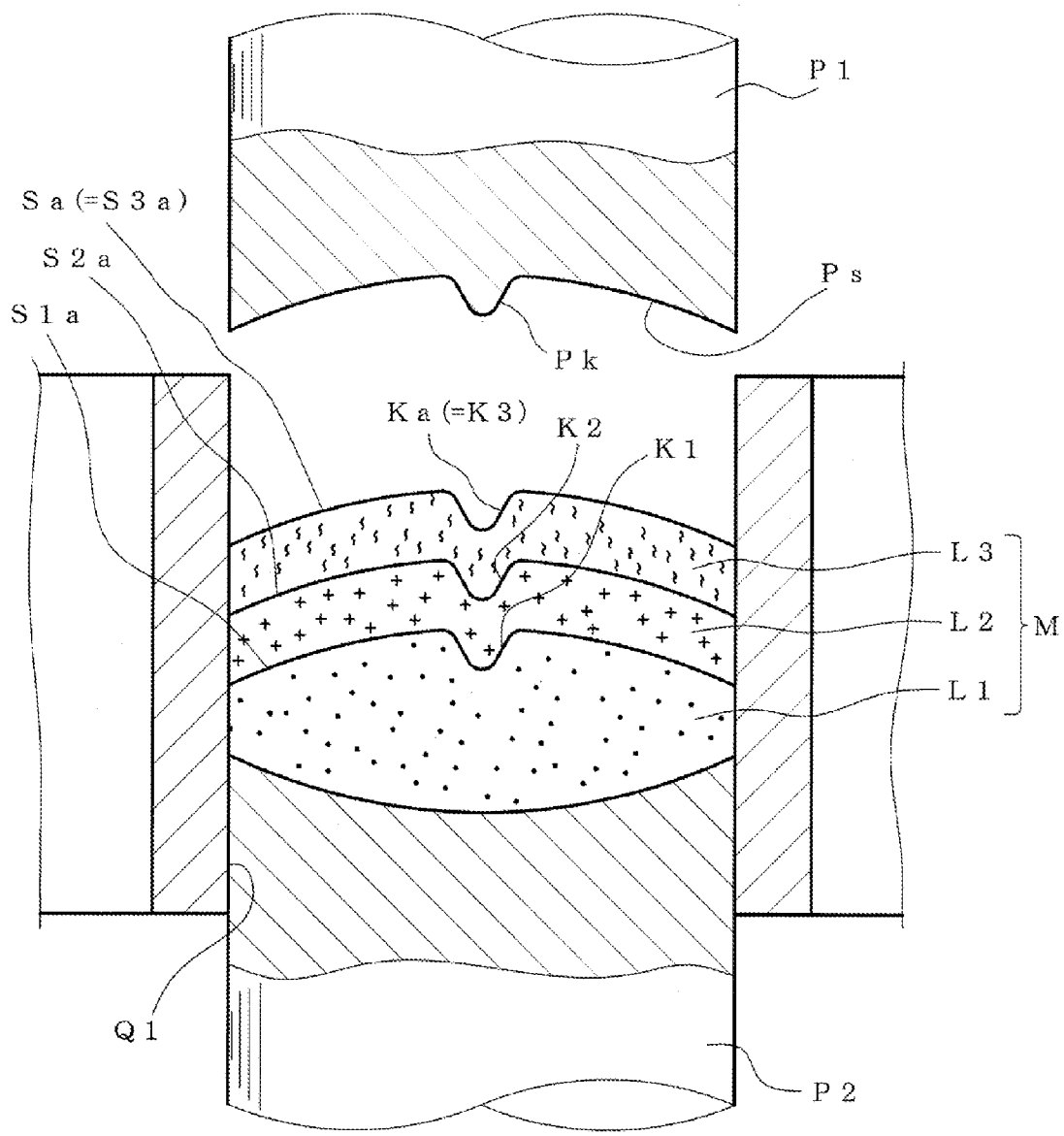
FIG. 2 is a sectional view showing a die and a pair of punches used for the production of the multilayer tablet of the present invention.

In the following, while an embodiment wherein a concave portion is formed on the upper surface as in FIG. 1(b), FIG. 2 is explained, the explanation of the concave portion when a concave portion is formed on a lower surface is also used here.

Explanations on the shape of each part of a tablet, and the shape of a concave portion directly quote the explanations of the shape of the punch which is the mold for tableting, the shape of the die, and the shape of the convex portion to be formed on the punch. That is, the outer shape of the tablet is the inner shape of the mold, the degrees of elevation of the upper surface and lower surface of the tablet are the degrees of depression of the upper punch and lower punch, respectively, and the shapes of all portions [pattern, depth, angle of slope surface of inside, width of opening] and the like of the concave portion of the tablet correspond to the shapes of all portions [pattern, height, angle of slope surface of outer surface, width of base part] and the like of the convex portion formed on a punch to form a concave portion, in a reversed relationship of concave and convex, like the relationship between the casting mold and the casting product.

The concave portion shows an increased adhesive force between layers according to the respective numerical values and forms, irrespective of the depth and pattern. However, in the present invention, as conditions that afford an adhesive force between layers useful for the quality control of the actual multilayer tablets, the depth of the concave portion is recommended to be not less than 0.1 mm. When the depth of the concave portion is less than 0.1 mm, a sufficient adhesive force for quality control between layers cannot be achieved even when the concave portion is a V-groove.

While the depth of the concave portion capable of effective suppression of layer separation varies depending on the embodiment of the concave portion (the below-mentioned hole, groove and the like), 0.1 mm-0.4 mm is preferable, 0.2 mm-0.4 mm is more preferable, and 0.3 mm-0.4 mm is particularly preferable from the aspects of the general thickness of each layer of the multilayer tablet and protrusion amount of the punch.

In addition, the width of the concave portion is preferably 0.6 mm-2.0 mm, more preferably 0.7 mm-1.7 mm.

The definition of the depth of the concave portion and the width of the concave portion is mentioned below by using FIG. 5.

While the form of the concave portion may be a sporadic hole concave portion as shown in FIG. 3(a), a groove-like concave portion as shown in FIG. 3(b) more increases the adhesive force between layers since the concave portion has a later inner wall area, and the contact surface between the inner wall surface of a concave portion and a protrusion of the next layer that enters thereinto, in the interface of layers becomes large. When a protrusion of the next layer that enters into the concave portion is a groove-like concave portion, the mechanical strength of the base part of the protrusion part becomes high, and shear fracture is preferably suppressed.

When inner wall area of the concave portion is increased, a plurality of the sporadic hole concave portion may be formed to ensure an inner wall area equivalent to the groove-like concave portion and the mechanical strength of the base part. However, taking note of the form of the convex portion of the upper punch that forms the concave portion, the convex portion is advantageously a ridge-line protrusion to form a groove-like concave portion, since it is easier to process than a sporadic form such as a conical protrusion and the like, has high strength and a long life.

Figure 4:
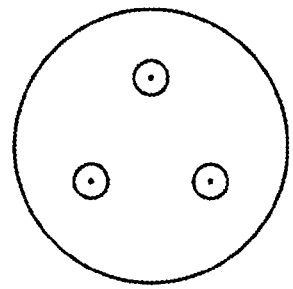
Figure 4:
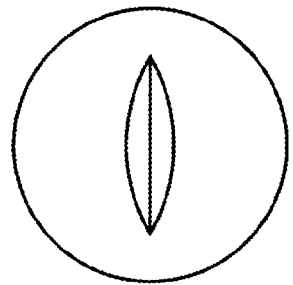
Figure 4:
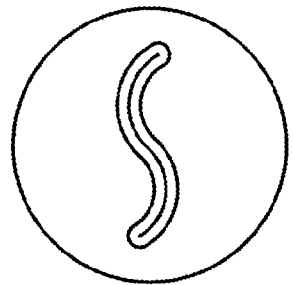
Figure 4:
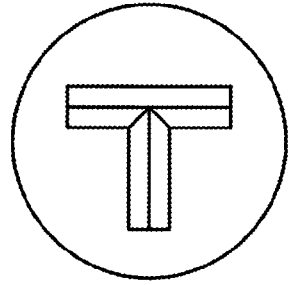

FIG. 4 shows examples of the pattern drawn by the concave portion when the surface on which the concave portion is formed (upper surface of the examples in this Figure) is viewed straight on.

FIG. 4(a) shows an example wherein the sporadic hole concave portion shown in FIG. 3(a) is formed in plurality. The center point of the circle showing each hole concave portion suggests a point on the bottom of the conical (sectional shape is V-shape) hole.

FIG. 4(b) shows an example of a groove-like concave portion along a straight line passing through the center point of the upper surface, wherein the groove-like concave portion is formed only in the central part of the upper surface. In contrast, in the example of FIG. 3(b), the groove-like concave portion extends from one point on the outer circumference of the upper surface through the center point to reach a point on the opposite side on the outer circumference.

FIG. 4(c) shows an example of a groove-like concave portion (V-shaped groove) along a curve passing through the center point of the upper surface. The straight line drawn to proceed along the center in the groove suggests a line on the bottom of the V-shaped groove.

FIG. 4(d) shows an example wherein a groove-like concave portion is formed to draw a letter of symbol on the upper surface. In the example of this Figure, a letter "T" has been drawn. The patterns of hole and groove in other Figures can also be considered letters and symbols, and they can be appropriately combined.

Figure 3:
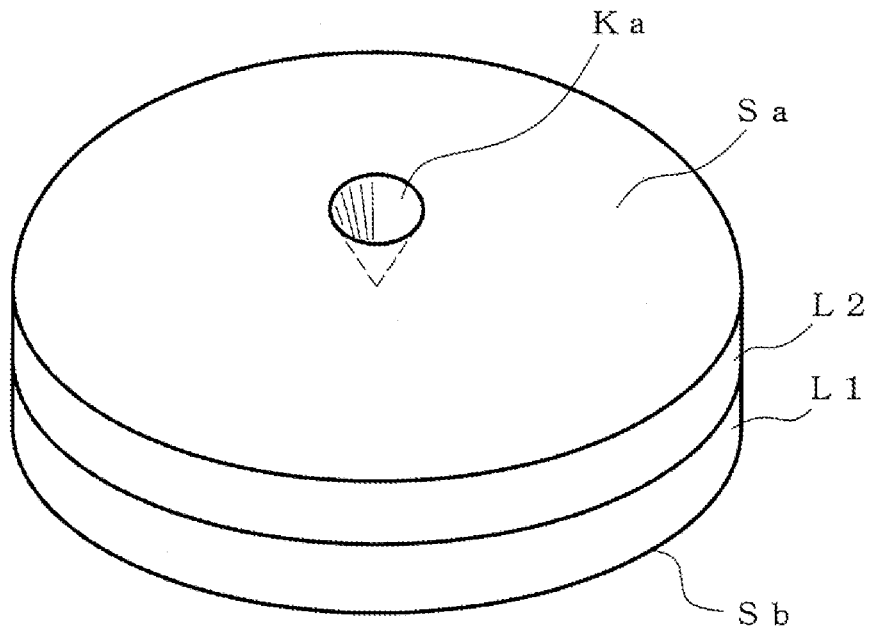
FIG. 3 is a perspective view showing a representative embodiment of a concave portion.
Figure 3:
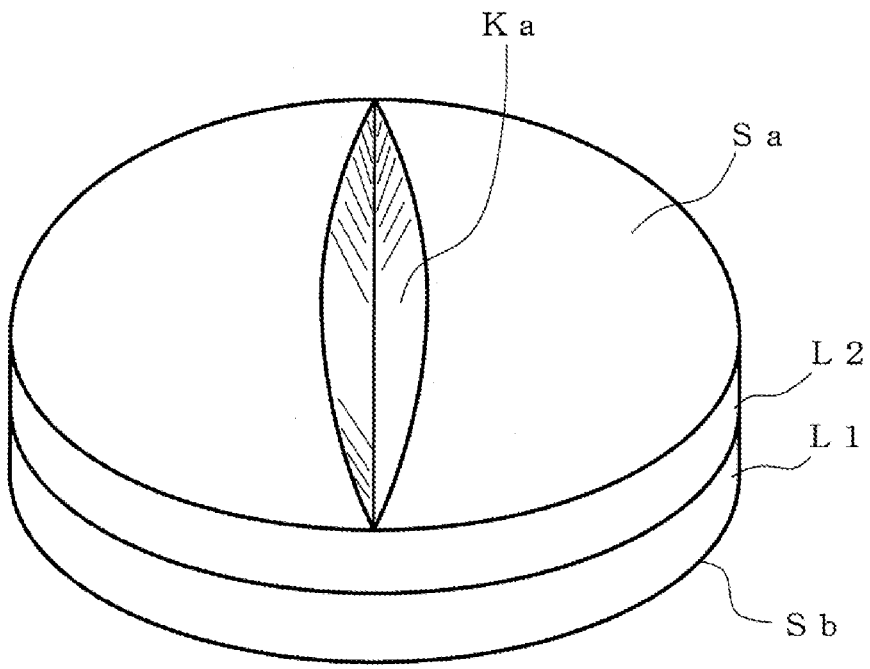

The examples shown in FIG. 3, FIG. 4 are mere representative examples, and the number, shape and configuration pattern of concave portion can be determined in consideration of strength of close adhesion, processability of upper punch, appearance and the like. Of the various patterns of these concave portions, a linear groove-like concave portion over the whole diameter of the tablet as in FIG. 3(b) is a preferable embodiment for efficiently conferring a suppressive effect to the whole tablet.

Figure 5:
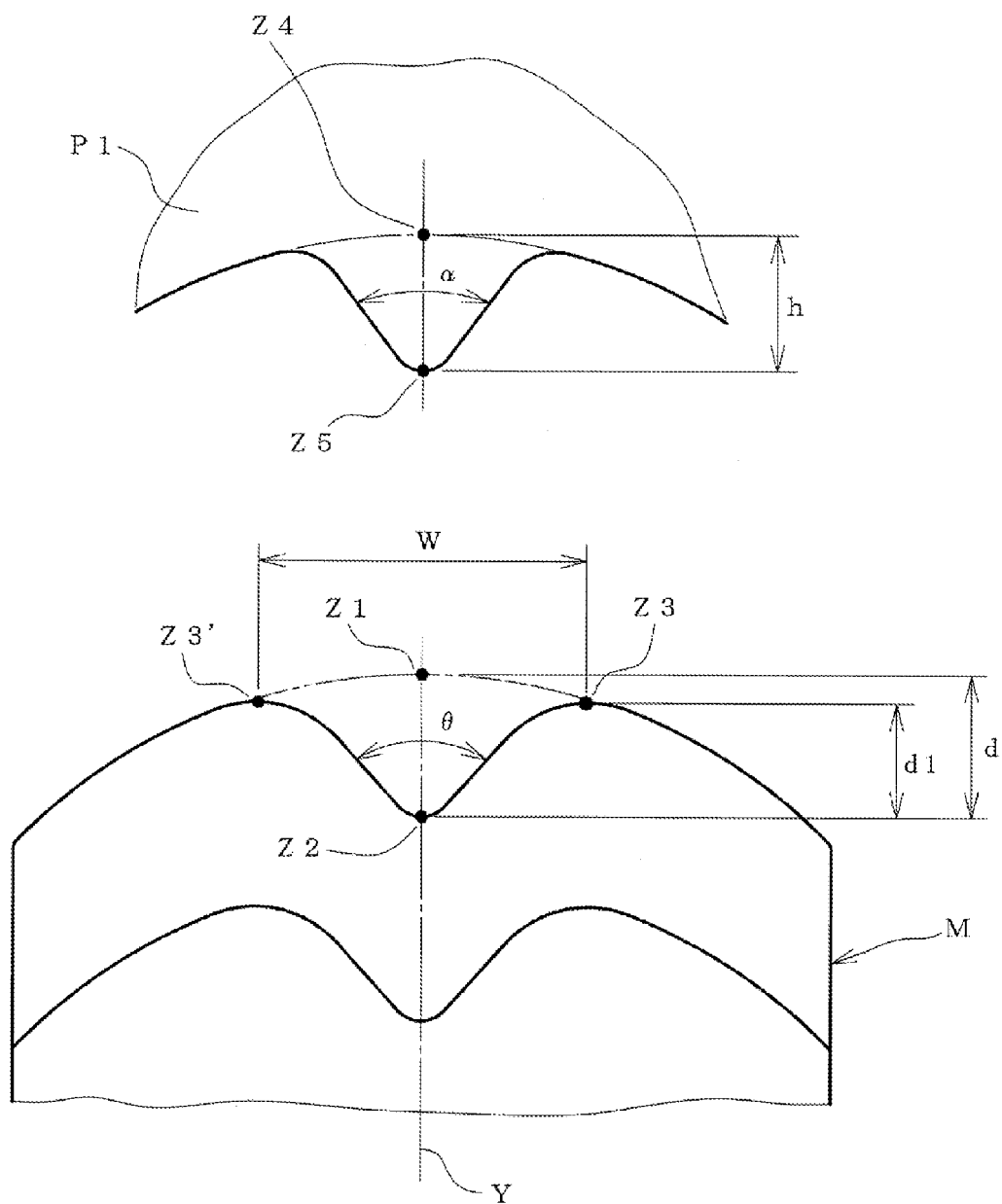
FIG. 5 shows sectional views showing the size of each portion of the concave portion when the upper surface of the multilayer tablet rises in a semispherical shape and the size of the convex portion of a punch to be defined at that time.

An actual concave portion that can be formed on the upper surface of said multilayer tablet preferably has a cross sectional shape of a V-shape (with appropriate roundness of bottom of V-shape and shoulder part of opening), as shown in FIG. 2 and FIG. 5, from the aspects of the mechanical strength, draft angle and the like of the convex portion formed on the punch. As mentioned above, moreover, the concave portion is more preferably a groove-like than a sporadic hole. Therefore, a preferable form of the concave portion is a V-shaped groove (cross sectional shape when cut perpendicularly to the longitudinal direction of the groove is a V-shaped groove).

However, when the convex portion of the upper punch is easily detached from the concave portion after tableting, layer separation also occurs easily. Therefore, the angle of the inside of the V-shape is preferably such an angle that permits easy detachment of the upper punch, confers high strength to the convex portion of the upper punch and a protrusion of the next layer that enters into the concave portion, and does not permit easy occurrence of layer separation. From these aspects, the angle θ of the inside of the V-shape shown in FIG. 5 is preferably 40-110 degrees, more preferably 50-100 degrees, particularly preferably 70-100 degrees. When the angle θ is less than 40 degrees, the convex portion of the upper punch and a protrusion of the next layer that enters into the concave portion become sharp and the problems of decreased strength, and a decreased powder amount that enters into the concave portion to lower the effect become marked. When the angle θ exceeds 110 degrees, the convex portion is easily detached from the concave portion after tableting and the layer separation occurs easily.

The concave portion formed on the upper surface of the multilayer tablet is different in the width and the angle of the inside of the V-shape from the letters and symbols formed as marks on the conventionally-known tablets.

When the upper surface of the multilayer tablet is a flat surface, the depth of the concave portion can be obtained by measuring the distance from the flat surface to the deepest part of the concave portion.

On the other hand, as shown in FIG. 5, when the upper surface of the multilayer tablet M is a curve rising semispherically, the depth of the concave portion in the context of the present invention is a distance d from a peak part Z1 on the design of the rising curve of the upper surface to a deepest part Z2 of the concave portion.

When the peak part Z1 is determined from an actual multilayer tablet, an intersection point Z1 of the curve of the upper surface and a center line Y of the concave portion only needs to be determined from a drawing of a section of the concave portion, as shown in FIG. 5. The same applies to a case when the upper surface has a different curve.

When a tablet has a general rise, the difference between the [distance d from peak part Z1 on the design of the curve of the rising upper surface to the deepest part Z2 of the concave portion] and [step (high-low difference) d1 between peak part Z3 (or Z3') at the shoulder of the opening of the concave portion and the deepest part Z2 of the concave portion] is not more than about 0.05 mm and is extremely small.

In addition, the height of the convex portion of the punch used for formation of a concave portion is also, like the depth of the concave portion. The height can be obtained by measuring the distance between the flat plane and the tip of the convex portion when the pressing-surface of the punch P1 is a flat plane. When the pressing-surface of the punch P1 is a semispherically recessed curve as shown in FIG. 5, it is a distance h from a peak part Z4 on the design of the recessed curve to the top Z5 of the convex portion.

The "width of the concave portion" is, as shown in FIG. 5, a distance W between the above-mentioned peak part Z3 on the shoulder of the opening of the concave portion, and a peak part Z3' of the other shoulder on the upper surface (or lower surface) of a multilayer tablet.

Whether a concave portion is formed on the upper surface of the layers other than the top layer of the multilayer tablet can be confirmed by observation of a tissue of the section of the multilayer tablet, particularly the state of the interface of the layers, by analyses using X-ray CT and terahertz waves, and the like. For example, the interface between layers can be specified based on a difference in the appearance caused by a difference in the formulations, and a minute space in the interface and, the concave portion can be found by tracking the interface. In addition, the concave portion can also be found by cutting the tablet and observing the cleavage face with a microscope The shape of the outer circumference, size, thickness and the number of layers of the multilayer tablet are similar to those of conventionally-known multilayer tablets. The shape of the outer circumference of multilayer tablets conventionally used as pharmaceutical products is mainly a circular shape or oval. When the shape of the outer circumference is a circular shape, the diameter is mainly 4 mm-10 mm, the thickness is mainly 2 mm-6 mm, and the number of the layers is mainly 2-3. The ratio of the thickness of respective layers varies depending on the property of the preparation and the like.

The multilayer tablet may be further applied with a known film coating on the surface of a core tablet. In this case, the depth of the concave portion is the depth immediately after tableting (core tablet).

Figure 6:
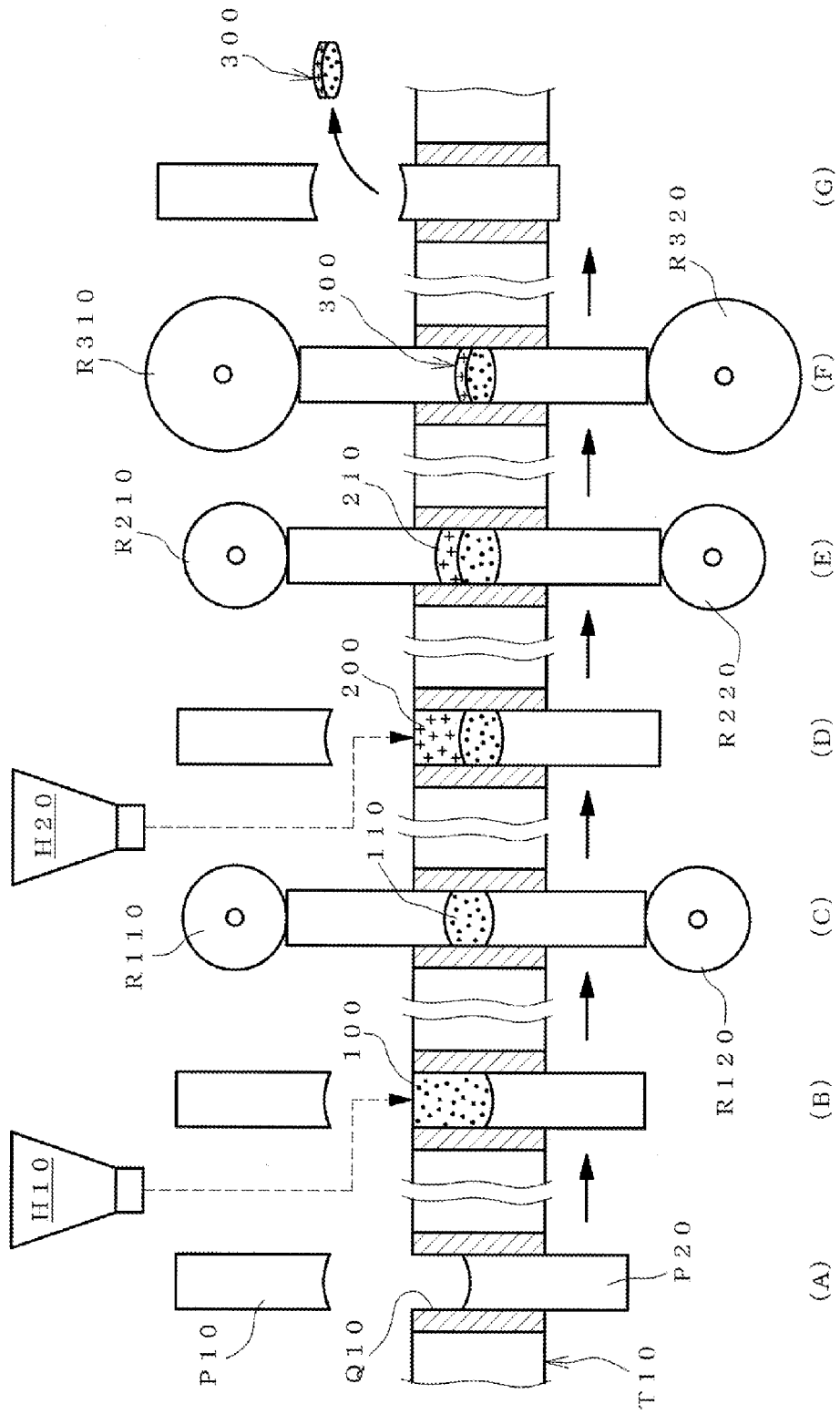
FIG. 6 shows a manner of sequentially forming respective layers of a multilayer tablet in a tableting step of a conventional multilayer tablet.
Figure 7:
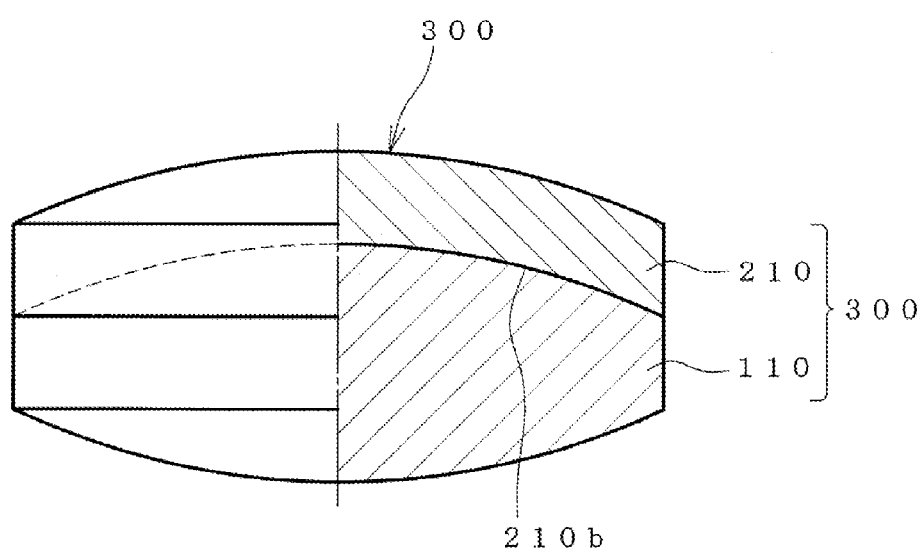
FIG. 7 shows the structure and the problem of a conventional multilayer tablet.
Figure 7:
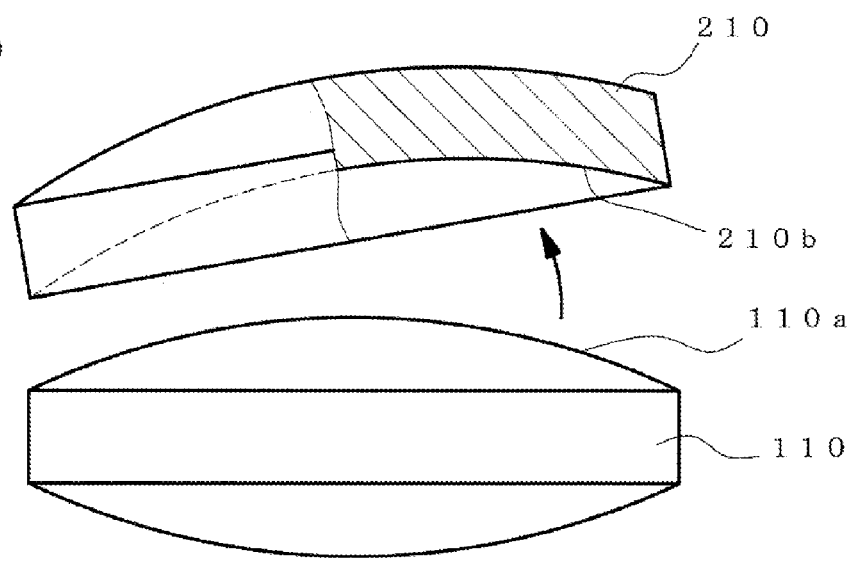

In the production method and the method for suppressing layer separation in the present invention, as shown in FIG. 2, a convex portion Pk with a height of not less than 0.1 mm to form the above-mentioned concave portion is formed on at least a mold surface (pressing surface) of the upper punch P1. Using the upper punch and in the same manner as in the tableting procedures for conventional multilayer tablets along FIG. 6 (A)-(G), powder materials for each layer are fed into a die, preliminary compression of each layer is performed with the upper and lower punches, and main compression is finally performed to complete a tabletting.

By such processing, a concave portion having the same shape with a depth of not less than 0.1 mm is formed on the upper surfaces of all layers. Then, as shown in FIG. 2, the materials of the next layer enter into the concave portion on the upper surfaces of all layers (L1, L2) other than top layer (L3), a multilayer structure wherein layer separation is suppressed can be formed.

The value of the preliminary compression and main compression of each layer may be similar to those used in the tabletting step of conventional multilayer tablets. For example, for a circular multilayer tablet with a diameter of 8 mm-9 mm and a thickness of 4 mm-6 mm, the preliminary compression of about 1-5 kN and the main compression of about 3-20 kN are preferable values.

The multilayer tablet may be a pharmaceutical product, quasi-drug, cosmetic, food (including supplement etc.), reagent and the like, and the use thereof is not limited.

The form of a multilayer tablet is suitable for, for example, pharmaceutical products.

The multilayer tablet can be used for preparations containing various active pharmaceutical ingredients.

Specific preferable examples of such active pharmaceutical ingredient include the following:

alogliptin or a salt thereof (preferably, benzoate), pioglitazone or a salt thereof (preferably, hydrochloride), metformin or a salt thereof (preferably, hydrochloride), and 2-((6-((3R)-3-aminopiperidin-1-yl)-3-methyl-2,4-dioxo-3,4-dihydropyrimidin-[(2H)-yl)methyl]-4-fluorobenzonitrile] or a salt thereof (preferably, succinate) which are useful as therapeutic drugs for diabetes [e.g., type 1 diabetes, type 2 diabetes, type 1.5 diabetes (LADA (Latent Autoimmune Diabetes in Adults)), gestational diabetes, impaired insulin secretion type diabetes, obese diabetes, impaired glucose tolerance (IGT (Impaired Glucose Tolerance)), IFG (Impaired Fasting Glucose), IFG (Impaired Fasting Glycaemia), borderline type diabetes], and the like;

candesartan cilexetil or a salt thereof, Azilsartan or a salt thereof, Azilsartan medoxomil or a salt thereof (preferably, potassium salt), hydrochlorothiazide or a salt thereof, and amlodipine or a salt thereof (preferably, hydrochloride), which are useful as therapeutic drugs for hypertension and the like.

Examples of the salt of the above-mentioned compound include a pharmacologically acceptable salt, such as a salt with inorganic acid, a salt with organic acid, a salt with basic or acidic amino acid and the like.

Preferable examples of the salt with inorganic acid include salts with hydrochloric acid, hydrobromic acid, nitric acid, sulfuric acid, phosphoric acid and the like.

Preferable examples of the salt with organic acid include salts with benzoic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like, and preferable examples of the salt with acidic amino acid include salts with aspartic acid, glutamic acid and the like.

The multilayer tablet may further contain an excipients conventionally used in the field of pharmaceutical preparation. Examples of the excipients include diluent, disintegrant, binder, lubricant, colorant, pH adjuster, surfactant, stabilizer, acidulant, flavor, fluidizer, coating base, coating excipients and the like. Unless particularly indicated, these additives are used in an amount conventionally employed in the field of pharmaceutical preparation.

Examples of the diluents include saccharides and sugar alcohols such as lactose, fructose, glucose, mannitol, sorbitol and the like; starches such as cornstarch, potato starch, wheat starch, rice starch, partly pregelatinized starch, pregelatinized starch, porous starch and the like; crystalline cellulose (e.g., microcrystalline cellulose); anhydrous calcium phosphate, precipitated calcium carbonate, calcium silicate and the like.

For the multilayer tablet, the excipient is preferably used at a content of 5-95 wt % per 100 parts by weight of the multilayer tablet of the present invention.

Preferable examples of the disintegrant include carboxymethylcellulose, carboxymethylcellulose calcium, carboxymethylstarch sodium, croscarmellose sodium, carmellose calcium, crospovidone, low-substituted hydroxypropylcellulose, hydroxypropylstarch and the like. The amount of the disintegrant to be used is preferably a content of 0.5-25 parts by weight per 100 parts by weight of the multilayer tablet of the present invention.

Preferable examples of the binder include hydroxypropylcellulose (e.g., grades: L, SL, SL-T, SSL (trade name); Nippon Soda Co., Ltd.), hydroxypropylmethylcellulose (e.g., hypromellose2910 (e.g., TC-5 (grades: MW, E, EW, R, RW) (trade name); Shin-Etsu Chemical Co., Ltd.)), polyvinylpyrrolidone (povidone), gum arabic hydroxypropylcellulose, hydroxypropylmethylcellulose, polyvinylpyrrolidone, gum arabic and the like.

For the multilayer tablet, the binder is preferably used at a content of 1-20 wt % per 100 parts by weight of the multilayer tablet of the present invention.

Preferable examples of the lubricant include magnesium stearate, calcium stearate, talc, sucrose esters of fatty acids, sodium stearyl fumarate and the like. The amount of said lubricant to be used is a content of 0.5-2 wt % per 100 parts by weight of the solid preparation.

Preferable examples of the colorant include food colors (e.g., Food Color Yellow No. 5, Food Color Red No. 2, Food Color Blue No. 2), food lake colors, red ferric oxide, yellow ferric oxide and the like.

Preferable examples of the pH adjuster include citrate, phosphate, carbonate, tartrate, fumarate, acetate, amino acid salt and the like.

Preferable examples of the surfactant include sodium lauryl sulfate, polysorbate 80, polyoxyethylene(160)polyoxypropylene(30)glycol and the like.

Preferable examples of the stabilizer include tocopherol, tetrasodium edetate, nicotinamide, cyclodextrins and the like.

Preferable examples of the acidulant include ascorbic acid, citric acid, tartaric acid, malic acid and the like.

Preferable examples of the flavor include menthol, peppermint oil, lemon oil, vanillin and the like.

Preferable examples of the fluidizer include light anhydrous silicic acid, hydrated silicon dioxide, talc and the like.

Preferable examples of the coating base include sugar coating base, water-soluble film coating base, enteric film coating base, sustained-release film coating base and the like.

Examples of the sugar coating base include sucrose. Furthermore, one or more kinds selected from talc, precipitated calcium carbonate, gelatin, gum arabic, pullulan, carnauba wax and the like may be used in combination.

Examples of the water-soluble film coating base include cellulose polymers such as hydroxypropylcellulose [e.g., grades: L, SL, SSL (trade name); Nippon Soda Co., Ltd.], hydroxypropylmethylcellulose [e.g., hypromellose2910, TC-5 (grades: MW, E, EW, R, RW) (trade name); Shin-Etsu Chemical Co., Ltd.]], hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; polysaccharides such as pullulan and the like, and the like.

Examples of the enteric film coating base include cellulose polymers such as hydroxypropylcellulose phthalate, hydroxypropylmethylcellulose acetate succinate, carboxymethylethylcellulose, cellulose acetate phthalate and the like; acrylate polymers such as methacrylate copolymer L [Eudragit L (trade name)], methacrylate copolymer LD [Eudragit L-30D55 (trade name)], methacrylate copolymer S [Eudragit S (trade name)] and the like; natural products such as shellac and the like, and the like.

Examples of the sustained-release film coating base include cellulose polymers such as ethylcellulose and the like; acrylate polymers such as aminoalkyl methacrylate copolymer RS [Eudragit RS (trade name)], ethyl acrylate.methyl methacrylate copolymer suspension [Eudragit NE (trade name)] and the like; and the like.

Preferable examples of the coating additive include light shielding agents such as titanium oxide and the like, fluidizers such as talc and the like; colorants such as red ferric oxide, yellow ferric oxide and the like; plasticizers such as polyethylene glycol (e.g., macrogol 6000), triethyl citrate, castor oil, polysorbates and the like; organic acids such as citric acid, tartaric acid, malic acid, ascorbic acid and the like; and the like.

Two or more kinds of the above-mentioned materials for film coating may be mixed at an appropriate ratio and used.

The multilayer tablet of the present invention can be safely administered orally or parenterally to a mammal (e.g., mouse, rat, rabbit, cat, dog, bovine, horse, monkey, human).

The dose of the multilayer tablet only needs to be an effective amount of a pharmaceutically active ingredient. This amount can be administered in one to several portions (e.g., 1-3 times) per day.

The present invention is explained in more detail in the following by referring to Examples, which are not to be construed as limitative.

As excipients for pharmaceutical preparations in the following Examples, the Japanese Pharmacopoeia 16th edition, the Japanese Pharmacopoeia Codex or Japanese Pharmaceutical Excipients 2003 compatible products were used.

EXAMPLES

Example 1

In the present Example, samples of a bilayer tablet having a V-shaped groove formed as a concave portion on the upper surface and/or the lower surface were produced, the angle and depth of the V-shaped groove were changed, and the degree of suppression of layer separation (the degree of increase of adhesive force between layers) was examined by comparison to a sample provided with no concave portion.
[Description of Bilayer Tablet Sample]

The shape of the outer circumference is a circular shape with a diameter of 8.5 mm, both the upper and lower surfaces have a spherically elevated face, the height of the rise from the end portion of the outer circumference is 1.4 mm, and the maximum total thickness is 5 mm.
[Forming Sample]

For tableting of sample, various upper punches and lower punches having a convex portion (ridgeline-like protrusion) corresponding to each shape of a V-shaped groove, which is formed on a pressing surface, were prepared. For comparison, upper punches and lower punches provided with no convex portion were also prepared.
(Formation of Mixture for the Second Layer (Top Layer)):

Alogliptin benzoate (13290 g), D-mannitol (45600 g) and micro crystalline cellulose (3900 g) were placed in a fluidized bed granulator [manufactured by POWREX CORPORATION, WFD-SG-60], and the mixture was granulated while spraying a solution (32500 g) of hydroxypropylcellulose (1950 g) in purified water, and the granules were subjected to a drying/milling step to give granules a. For reference, a production method of alogliptin benzoate is shown after said Example.

The obtained granules a (60180 g) were mixed with crystalline cellulose (7250 g), croscarmellose sodium (4350 g) and magnesium stearate (725.0 g) to give mixture A for the second layer.
(Formation of Mixture for the First Layer (Bottom Layer)):

Pioglitazone hydrochloride (6777 g), lactose monohydrate (44070 g) and croscarmellose sodium (2706 g) were placed in a fluidized bed granulator [manufactured by POWREX CORPORATION, WFD-SG-60], and the mixture was granulated while spraying a solution (27920 g) of hydroxypropylcellulose (1394 g) in purified water, and then sequentially spraying a suspension (74130 g) of hydroxypropylcellulose (1558 g) and lactose monohydrate (14760 g) in purified water, and the granules were subjected to a drying/milling step to give granules b.

The obtained granules b (66050 g) were mixed with croscarmellose sodium (2075 g) and magnesium stearate (273.6 g) to give mixture B for the first layer.
(Tableting into Bi Layer Tablet):

Mixture B was tableted by a bilayer tabletting machine [manufactured by HATA IRON WORKS CO., LTD., HT-X65LD-UW/2L] (tablet size: diameter 8.5 mm, compression pressure 1 kN/punch) to produce a tablet for the first layer (mass: 180 mg/tablet). Subsequently, mixture A was filled in the tabletting machine and compressed (compression force 10 kN/punch) to laminate the second layer on the first layer, whereby a bilayer tablet containing alogliptin benzoate (17 mg)/pioglitazone hydrochloride (16.53 mg) per tablet (mass: 280 mg/tablet) was obtained.

The detail of the formulation amount of each layer per tablet is shown in the following Table 1.

TABLE 1

| | component name | formulation amount (mg/T) |
|---|---|---|
| second layer (uppermost layer) | alogliptin benzoate | 17 |
| | D-mannitol | 58.5 |
| | microcrystalline cellulose | 15 |
| | hydroxypropylcellulose | 2.5 |
| | croscarmellose sodium | 6 |
| | magnesium stearate | 1 |
| first layer (lowermost layer) | Pioglitazone hydrochloride | 16.53 |
| | lactose monohydrate | 143.49 |
| | croscarmellose sodium | 12.06 |
| | hydroxypropylcellulose | 7.2 |
| | magnesium stearate | 0.72 |
| | total | 280 mg |

The form of the concave portion is a linear V-shaped groove over the whole diameter of the tablet, the angle of the inside of the V-shape is (70 degrees, 100 degrees), and the depth of the V-shaped groove is (0.1 mm, 0.2 mm, 0.3 mm, 0.4 mm).

For comparison, a sample without a concave portion was also produced.

[Test Method for Measuring Degree of Layer Separation]

To measure the degree of layer separation, a test equipment having a structure similar to that of the equipment defined in the "Test method for tablet friability test" of the Japanese pharmacopeia 15th Edition, and resemblingly different only in the materials and size of the drum was produced.

The produced test equipment has a hollow drum having a horizontally-held rotation axis and rotationable by an electric motor. A sample tablet is placed in the drum, the drum is rotated given times at a given speed to make the tablet go up and fall in the drum, and the degree of layer separation of the multilayer tablet due to the impact is observed. One partition plate is set inside the drum from the center of rotation to the outer circumference wall, by which the tablet is lifted.

In the equipment defined in the Japanese pharmacopeia, the material of the drum is plastic and the inner diameter is about 287 mm and the depth is about 38 mm. In the test equipment produced in the present Example, a part of the material of the drum inner wall is stainless, and the inner diameter is about 500 mm and the depth is about 60 mm.

To examine the degree of layer separation, samples (10 tablets) were fed into the drum of the above-mentioned test equipment, and rotated for 10 min at a rotating speed of 30 rpm/min to examine the number of tablets showing layer separation. This test was performed twice (n=2) in total.

As the results of the above-mentioned tests, the depth of the V-shaped groove and the angle of the inside of the V-shape in each sample, and the number of tablets showing layer separation are shown in the following Table 2.

TABLE 2

| tablet sample No. | upper surface | | lower surface | | number of tablets with phase separation |
|---|---|---|---|---|---|
| | depth of concave part (mm) | angle (degrees) | depth of concave part (mm) | angle (degrees) | |
| 1 | 0.1 | 70 | 0.1 | 70 | 14 |
| 2 | 0.3 | 70 | 0.3 | 70 | 11 |
| 3 | 0.4 | 70 | 0.4 | 70 | 9 |
| 4 | 0.4 | 100 | 0.4 | 100 | 7 |
| 5 | no concave part | | 0.1 | 70 | 20 |
| 6 | no concave part | | 0.3 | 70 | 12 |
| 7 | no concave part | | 0.4 | 70 | 13 |
| 8 | no concave part | | 0.4 | 100 | 15 |
| 9 | no concave part | | no concave part | | 15 |
| 10 | 0.1 | 70 | no concave part | | 11 |
| 11 | 0.2 | 70 | no concave part | | 8 |
| 12 | 0.3 | 70 | no concave part | | 12 |
| 13 | 0.4 | 70 | no concave part | | 1 |
| 14 | 0.4 | 100 | no concave part | | 7 |

In the above-mentioned Table 2, a comparison of sample. No. 9 provided with no concave portion on both surfaces, sample Nos. 5-8 provided with a concave portion only on the lower surface, and sample Nos. 10-14 provided with a concave portion only on the upper surface has clarified that a higher effect can be obtained for suppressing layer separation by providing a concave portion on the upper surface rather than the lower surface.

In addition, from the results of sample No. 9 provided with no concave portion on both surfaces and sample Nos. (1-3), (5-7) and (10, 11, 13) with varying depths of the concave portion, it has been clarified that a deeper concave portion tends to provide a higher effect for suppressing layer separation.

Furthermore, from the results of sample No. 9 provided with no concave portion on both surfaces, and sample Nos. (3, 4), (7, 8) and (13, 14) with varying angles of the inside of the V-shape of the concave portion, it has been clarified that the angles of the inside of the V-shape of 70 degrees and 100 degrees produce no remarkable difference in the layer separation suppressive effect.

Reference Example 1

A Production Example of alogliptin benzoate (4a) in the following formulas 1 is shown below.

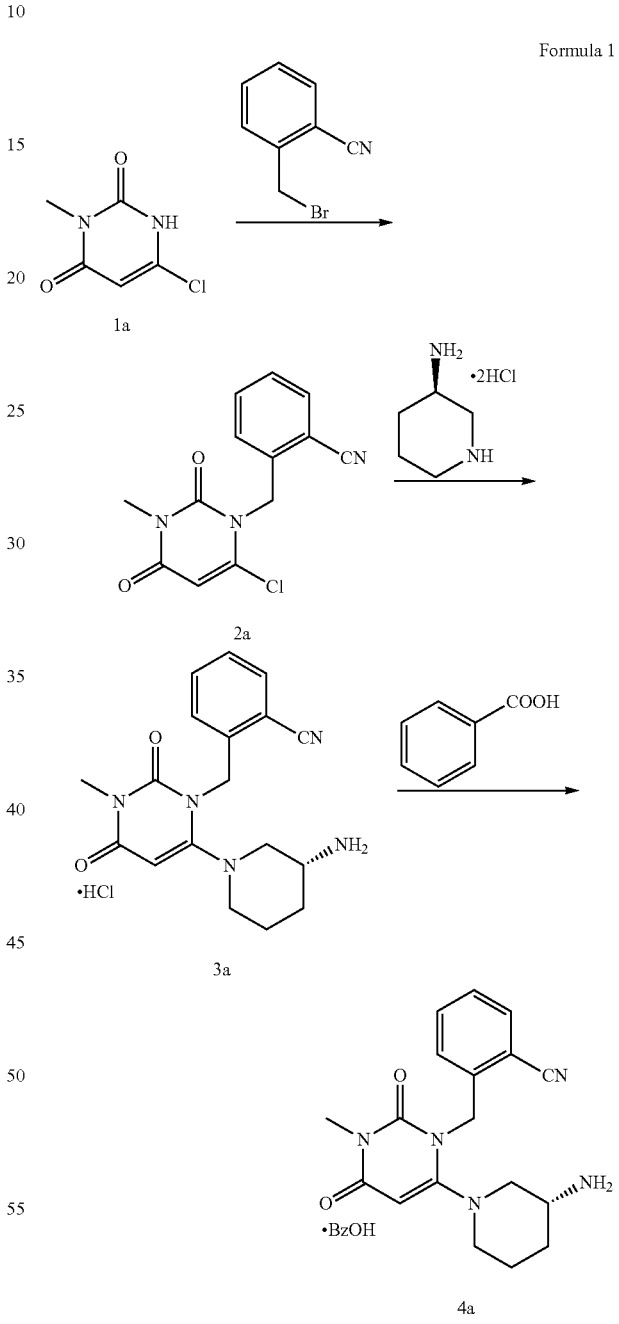

Formula 1

Production step of 2-((6-chloro-3-methyl-2,4-dioxo-3,4-dihydropyrimidin-1(2H)-yl)methyl)benzonitrile (2a) in the above-mentioned formula 1

Toluene (1.7-fold amount), α-bromotoluoylnitrile (1.1 equivalents, 1.34 wt.), 6-chloro-3-methyluracil (1a) (1 equivalent, 1 wt.), and N-methylpyrrolidone (NMP; 3-fold amount) were heated to an inside temperature of 45-55° C. Diisopropylethylamine (Hunig base, 1.5 equivalents, 1.21 wt.) was added while keeping the inside temperature of 45-55° C.

The mixture was stirred at 45-55° C. for 3-7 hr or until completion of the reaction.

Then, the solution was cooled to 25-35° C., and isopropanol (5.8-fold amount, 4.6 wt.) was added while keeping 25-35° C. Water (4-fold amount) was added while keeping the inside temperature of 25-35° C., and the mixture was stirred for about 30 min. The mixture was cooled to 0-5° C., and thereafter stirred for at least 1 hr. The obtained slurry was filtered, washed with isopropanol (4.4-fold amount, 3.5 wt.) cooled to 0-5° C., and vacuum dried at not more than 60° C. to give the above-mentioned compound (2a).

Production step of (R)-2-((6-(3-aminopiperidin-1-yl)-3-methyl-2,4-dioxo-3,4-dihydropyrimidin-1(2H)-yl)methyl)benzonitrile (3a) in the above-mentioned formula 1

The above-mentioned compound (2a) was reacted with 1.1 equivalents of (R)-3-aminopiperidine dihydrochloride in isopropanol and water at 58-68° C. until the completion of the reaction (e.g., 8-17 hr). Potassium carbonate (2 equivalents) was added in portions while keeping 58-68° C. (for about 2-5 hr). After cooling to 45-55° C., the mixture was stirred for about 2-5 hr. The inorganic salt was removed by filtration, and the filtration cake was washed with heated (e.g., 45-55° C.) isopropanol. THF was added, and the mixture was acidified with 35% hydrochloric acid while keeping the inside temperature of 10-20° C. The obtained slurry was cooled to 0-5° C., stirred until crystal grew (e.g., not less than 1 hr), and thereafter filtered. The filtration cake was washed with isopropanol (6-fold amount) and dried until HCl salt of the above-mentioned compound (3a) was obtained as a white crystalline solid.

Production Step of Benzoate (4a) of Compound (3a) in the Above-Mentioned Formula 1

The HCl salt of the above-mentioned compound (3a) was dissolved in water at 35-45° C. and washed with isopropyl acetate to remove the dimer. Isopropyl acetate was added to the obtained aqueous phase, and the mixture was heated to 45-55° C., and solid potassium carbonate was added while keeping the batch temperature at 45-55° C. to liberate the base from the aqueous phase into the organic phase. Each phase was separated at 55-65° C., and the organic phase was washed with 23% aqueous sodium chloride solution, and residual potassium salt was removed. The organic solvent was concentrated to about 3-fold under reduced pressure. Alcohol (4-fold amount) was added, and the solution was concentrated to about 4-fold under reduced pressure. A 4-fold amount of alcohol was added again, and the solution was concentrated to about 4-fold again under reduced pressure. The obtained solution was passed through a dust removal filter to remove the precipitated sodium chloride and fine particles. A solution (65-70° C.) of benzoic acid in hot ethanol was added, and the solution was maintained at 65-70° C. Then, the solution was cooled to 0-5° C. and stirred for not less than 1 hr to give a crystal. The solution was filtered, and the filtrate was washed with alcohol. Then, the wet cake was dried at 40-50° C. to give benzoate of the above-mentioned compound (3a) (alogliptin benzoate) (4a) as a white crystalline solid.

Reference Example 2

A Production Example of 2-((6-((3R)-3-aminopiperidin-1-yl)-3-methyl-2,4-dioxo-3,4-dihydropyrimidin-1(2H)-yl)methyl)-4-fluorobenzonitrile succinate (4b) in the following formulas 2 is shown below.

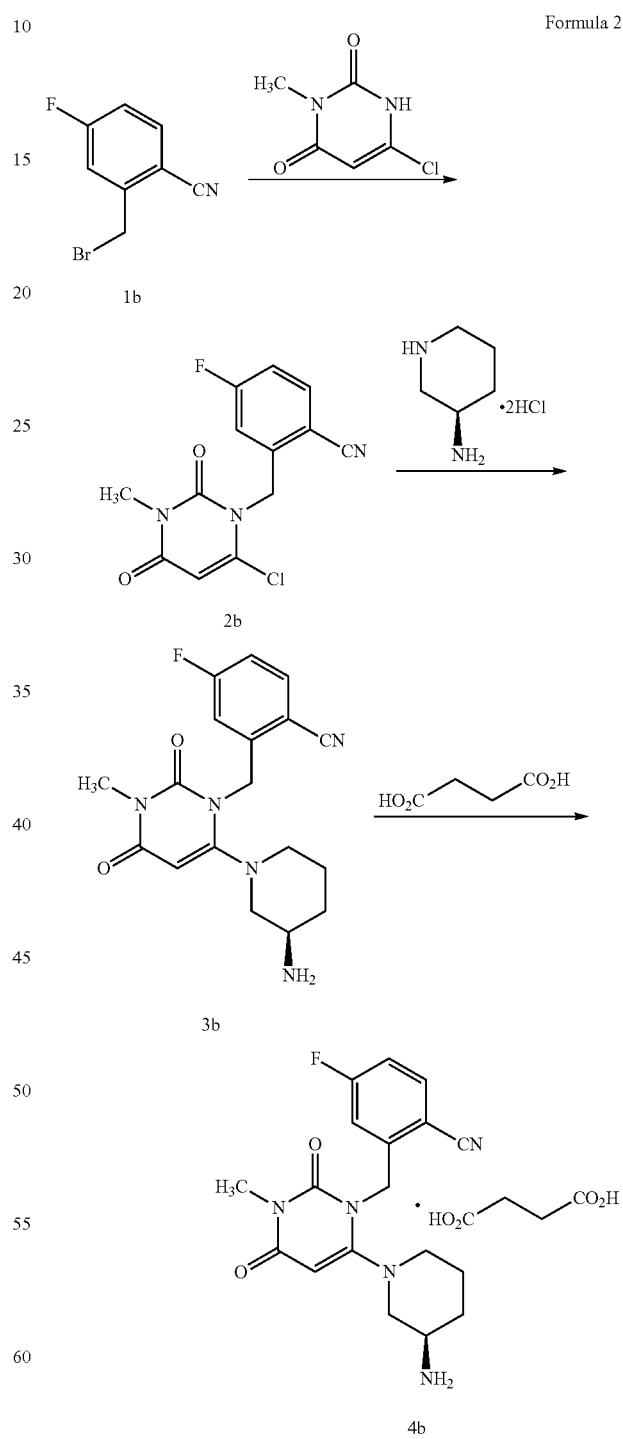

Formula 2

Production step of 2-((6-chloro-3-methyl-2,4-dioxo-3,4-dihydropyrimidin-1(2H)-yl)methyl)-4-fluorobenzonitrile (2b) in the above-mentioned formula 2

Ethyl acetate (3.5-fold amount), 2-(bromomethyl)-4-fluorobenzonitrile (1b) (1 equivalent, 1 wt.), 6-chloro-3-methyluracil (1.05 equivalents, 0.79 wt.), N-methylpyrrolidone (NMP; 3.5-fold amount), and diisopropylethylamine (Hunig base, 2.1 equivalents, 1.27 wt.) were heated to an inside temperature of 60-70° C.

The mixture was stirred at 60-70° C. for 2-4 hr or until the completion of the reaction.

Then, the solution was cooled to 40-50° C., stirred for at least 30 min, isopropanol (1.5-fold amount) and water (3.5-fold amount) were added while keeping at 40-50° C., and then stirred for at least 1 hr. The solution was cooled to 20-30° C., and then stirred for at least 1 hr. The solution was cooled to 0-10° C., and then stirred for at least 1 hr. The obtained slurry was filtered, washed with isopropanol (4.0-fold amount) cooled to 0-10° C., and vacuum dried at 45-55° C. to give the above-mentioned compound (2b).

Production step of 2-((6-((3R)-3-aminopiperidin-1-yl)-3-methyl-2,4-dioxo-3,4-dihydropyrimidin-1(2H)-yl)methyl)-4-fluorobenzonitrile (3b) in the above-mentioned formula 2

The above-mentioned compound (2b) (1 equivalent, 1 wt.), (R)-3-aminopiperidine dihydrochloride (1.1 equivalents, 0.65 wt.), potassium carbonate (2.5 equivalents, 1.18 wt.), isopropanol (5.0-fold amount), and water (1.5-fold amount) were reacted at 65-75° C. until the completion of the reaction (e.g., 3-7 hr). Potassium carbonate (7.05 equivalents, 3.32 wt.) and water (5.5-fold amount) were added at 65-75° C., and the mixture was stirred for about 30 min, and each phase was separated at 50° C.-70° C. The organic solvent was concentrated about 5-fold under reduced pressure. Water (5-fold amount) was added to the solution, and the mixture was concentrated to about 5-fold under reduced pressure. The solution was stirred at 55° C.-75° C. for about 40 min. The solution was cooled to 20° C.-30° C., and then stirred for at least 1 hr. The solution was cooled to 0-10° C., and then stirred for at least 1 hr. The obtained slurry was filtered, and the filtrate was washed with water (2.0-fold amount) cooled to 0-10° C. and vacuum dried at 45-55° C. to give the above-mentioned compound (3b).

Production Step of Succinate (4b) of the Above-Mentioned Compound (3b) in the Above-Mentioned Formula 2

Compound (3b), tetrahydrofuran (6.0-fold amount), isopropanol (3.0-fold amount) and water (0.6-fold amount) were heated to 55-65° C. A solution (20° C.-30° C.) of succinic acid in tetrahydrofuran was added and the solution was stirred at 55-65° C. for about 15 min.

The solution was cooled to 20-30° C., and stirred for at least 1 hr. The solution was cooled to 0-10° C., and then stirred for at least 1 hr. The obtained slurry was filtered, and the filtrate was washed with isopropanol (6.0-fold amount). The obtained wet crystal was dried at 65-75° C. to give succinate (4b) of the above-mentioned compound (3b) as a white crystalline solid.

INDUSTRIAL APPLICABILITY

As mentioned above, the present invention has enabled provision of a multilayer tablet showing suppressed layer separation and a production method thereof.

This application is a National Stage application of PCT/JP2012/055382, filed Mar. 2, 2012 which claims priority from patent application No. 2011-046617 filed in Japan (filing date: Mar. 3, 2011), the contents of which are incorporated in full herein.

The invention claimed is:

1. A multilayer tablet comprising a shape having a lower surface, an upper surface, and a peripheral side surface which defines each outer circumference of said lower and upper surfaces, wherein said upper surface comprises a groove-like concave portion having a depth of not less than 0.1 mm, and wherein the layer having said upper surface having the concave portion is the top layer, and the multilayer tablet being produced by a tableting process comprising a tableting step, wherein a die having an inner surface to define said peripheral side surface, a lower punch having a mold surface for pressing to form said lower surface, and an upper punch having a mold surface for pressing to form said upper surface are used in the tableting step, on the mold surface of the upper punch, a convex portion with a height of not less than 0.1 mm for forming a concave portion on the upper surface of the multilayer tablet, all layers in the multilayer tablet are directly pressed by the same upper punch during successive tableting, whereby a concave portion having the same shape as the concave portion of the upper surface is also formed in an upper side surface of each layer other than said top layer, and a material of the layer above each layer protrudes from the under side surface of the layer above into the concave portion of each layer other than said top layer, wherein the multilayer tablet comprises an active pharmaceutical ingredient in each layer, and said groove-like concave portion is a V-shaped groove, and the V-shaped groove has an inside angle of the V-shape of 70 degrees to 100 degrees.

2. The multilayer tablet according to claim 1, wherein the V-shaped groove-like concave portion is present along a straight line or a curve passing through the center point of the upper surface having said concave portion, when the surface is viewed straight on.

3. The multilayer tablet according to claim 2, wherein said groove-like concave portion runs from one point on an outer circumference of said upper surface, passes through the center point of the upper surface, and reaches a point on the opposite side of the outer circumference.

4. A method of producing the multilayer tablet according to claim 1, comprising
a step of sequentially laminating respective layers in said multilayer tablet on a mold surface of the lower punch, and tableting by an upper punch,
at least the upper punch has a convex portion having a height of not less than 0.1 mm on its mold surface,
said tableting step has a step of pressing all layers in said multilayer tablet by said upper punch, and
said pressing step forms a multilayer structure wherein a concave portion having the same shape with a depth of not less than 0.1 mm is formed on an upper punch side surface of all layers, and the materials of the next layer are protruding into the concave portions of all layers other than the top layer.

5. A method for suppressing layer separation of the multilayer tablet according to claim 1, comprising forming the V-shaped groove-like concave portion having the depth of not less than 0.1 mm on the upper surface and the upper side surface of each layer of the multilayer tablet.

6. The method according to claim 5, wherein, when forming said multilayer tablet by sequentially laminating respective layers in a multilayer tablet on a mold surface of the lower punch, and tableting with the upper punch, at least the upper punch has, on its mold surface, a convex portion having a height of not less than 0.1 mm, all layers in said multilayer tablet are pressed by said upper punch, whereby a multilayer structure wherein a concave portion having the same shape with a depth of not less than 0.1 mm is formed on an upper punch side surface of all layers, and the materials of the next layer are protruding into said concave portions of all layers other than the top layer.

\* \* \* \* \*